United States Patent [19]

McIntosh

[11] Patent Number: 6,042,843

[45] Date of Patent: *Mar. 28, 2000

[54] BACULOVIRUS FOR THE CONTROL OF INSECT PESTS

[75] Inventor: Arthur H. McIntosh, Columbia, Mo.

[73] Assignee: The United States of America as represented by the Secretary of Agriculture, Washington, D.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/756,301

[22] Filed: Nov. 25, 1996

[51] Int. Cl.[7] .............................. A01N 25/00; A01N 63/02
[52] U.S. Cl. ...................... 424/405; 424/408; 424/417; 424/406; 435/235.1; 435/237
[58] Field of Search ...................... 424/405, 406, 424/408, 409, 410, 417, 93.6; 435/235.1, 237, 239

[56] References Cited

U.S. PATENT DOCUMENTS

| | | | |
|---|---|---|---|
| 4,328,203 | 5/1982 | Spence et al. | 424/16 |
| 4,911,913 | 3/1990 | Hostetter et al. | 424/93 |
| 5,405,770 | 4/1995 | McIntosh | 435/235.1 |

FOREIGN PATENT DOCUMENTS 9636221   11/1996   WIPO .

OTHER PUBLICATIONS

K. Padmavathamma & G. K. Veeresh "Effect of larval age and dosage of nuclear polyhedrosis virus on the susceptibility of diamondback moth, *Plutella xylostella*" Entomol. exp. appl. 60: 39–42, 1991, Kluwer Academic Publishers 1991.
Varma et al. J. Res. Punjab Agric. Univ. 14(3) pp. 304–308, 1977.
Biever et al. J. Invertebr Pathol 44(1) pp. 117–119, 1984.
Kadir et al. J. Invertebr. Pathol. 53(1) pp. 113–115, 1989.
Wilding Diamondback Month Mgmt.—Mar. 11–15 1985 Proceedings—Taiwan pp. 219–232, 1986.

*Primary Examiner*—Neil S. Levy
*Attorney, Agent, or Firm*—M. Howard Silverstein; Randall E. Deck; John D. Fado

[57] ABSTRACT

A novel *Plutella xylostella* baculovirus (PxMNPV) which is useful for the control of insect pests has been isolated. A variety of insect pests may be controlled by application of an insecticidally effective amount of the baculovirus to the locus or vicinity of the target insect.

8 Claims, No Drawings

3,042,843

BACULOVIRUS FOR THE CONTROL OF INSECT PESTS

BACKGROUND OF THE INVENTION

1. Field of the Invention

The invention relates to a *Plutella xylostella* baculovirus which may be used for the biological control of insect pests.

2. Description of the Prior Art

Chemical pesticides and fungicides are the most commonly used control agents for forest and agricultural insect pests and fungal diseases. In excess of 350 billion pounds of these agents are used annually in the United States to control pests and diseases in forestry, agriculture, and residential areas. Unfortunately, broad spectrum insecticides and fungicides have adverse impacts not only on their target organisms but also on beneficial insects and fungi and, consequently, on the entire ecosystem. Pest insects may also acquire resistance to such chemicals so that new pest insect populations can develop that are resistant to these pesticides. Furthermore, chemical residues pose environmental hazards and possible health concerns.

Interest in biological insect and fungal control agents is growing as a consequence of concerns regarding chemical pesticide use. The biological control of insect pests presents an alternative means of pest control which can play a role in integrated pest management and reduce dependence on chemical pesticides. Generally, natural control agents have little adverse ecological impact due to their specificity for the target host. Long term environmental hazards and health concerns are not a factor with biological control agents because chemical residues are not present. However, biological control agents may suffer from several disadvantages in comparison to chemical pesticides, including cost of production, efficacy, and stability.

Viruses that cause natural epizootic diseases within insect populations are among the entomopathogens which have been developed as biological pesticides. A variety of viruses, including baculoviruses, are known to be valuable biological control agents for insects. Baculoviruses are a large group of viruses which are infectious only in arthropods (L. K. Miller, Virus Vector for Genetic Engineering in Invertebrates, in "Genetic Engineering in the Plant Sciences", N. Panopoulous, Ed., Praeger Publ., N.Y., pp. 203–224, 1981; Carstens, 1980, "Baculoviruses—Friend of Man, Foe of Insects?," Trends and Biochemical Science, 52:107–110; Harrap and Payne, "The Structural Properties and Identification of Insect Viruses" in Advances in Virus Research, M. A. Lawfer, F. B. Bang, K. Maramorosh and K. M. Smith, Eds., Vol. 25, pp. 273–355, Academic Press, New York, 1979).

In nature, infection is initiated when an insect ingests food contaminated with baculovirus particles, typically in the form of occlusion bodies (OB) which are composed of multiple viral particles embedded within a virus-encoded proteinaceous crystal. When consumed by susceptible insects, the protein crystal of the occlusion bodies is dissolved in the alkaline environment of the insect midgut, releasing individual virus particles which invade epithelial cells lining the midgut. Within the cell, the baculovirus migrates to the nucleus where replication takes place. Generally, two forms of baculovirus, occluded and extracellular virus (ECV), are produced during viral replication. Both of these viral particles as well as the OB itself possess envelopes. Initially, extracellular virus (ECV) is produced, acquiring an envelope as it buds out from the surface of the cell. This extracellular virus (ECV) can then infect other cells within the insect, including fat body cells, epidermal cells, and hemolymph. Following this initial stage of infection, virus is produced which is occluded in occlusion bodies. Occlusion body formation continues until the cell ultimately dies or lyses. Some baculoviruses infect virtually every tissue in the host insect so that at the end of the infection process, the entire insect is liquified, releasing extremely large numbers of occlusion bodies which are then responsible for spreading the infection to other insects. See "The Biology of Baculoviruses," R. G. Granados and B. A. Federici, Eds., Vol. I and II, CRC Press, Boca Raton, Fla., 1986.

Many baculoviruses infect insects which are pests of commercially important agricultural and forestry crops. Such baculoviruses are therefore potentially valuable as biological control agents. To date, several different baculoviruses have been registered for use as insecticides by the U.S. Environmental Protection Agency. One of these, *Autographa californica* multiple nuclear polyhedrosis virus (AcMNPV), is well recognized for its use as a biocontrol agent because of its wide host range within the order Lepidoptera. Another baculovirus, *Anagrapha falcifera* multiple nuclear polyhedrosis virus (AfMNPV), was recently isolated from a celery looper and differs from AcMNPV both in its REN pattern and its greater infectivity for Heliothis subflexa larvae. AfMNPV is approximately equally infectious for both *H. zea* and *H. virescens* larvae and possesses a wide range infecting over 30 species from 10 families in the order Lepidoptera.

SUMMARY OF THE INVENTION

We have now discovered a novel *Plutella xylostella* baculovirus which is useful for the control of insect pests. A variety of insect pests may be controlled by application of an insecticidally effective amount of the baculovirus to the locus or vicinity of the target insect.

In accordance with this discovery, it is an object of this invention to provide a novel baculovirus which is useful as a biological control agent for the control of insect pests.

It is also an object of the invention to provide a baculovirus which is effective for the control of a wide range of insect pests, including *Plutella xylostella*, without the use of chemical insecticides.

Another object of the invention is to provide a method for controlling insect pests using a baculovirus as a biological control agent.

Other objects and advantages of this invention will become readily apparent from the ensuing description.

DETAILED DESCRIPTION OF THE INVENTION

The novel *Plutella xylostella* baculovirus of this invention is a multiple nuclear polyhedrosis virus belonging to the family Baculoviridae, and is referred to as PxMNPV. This baculovirus was originally isolated from larvae of the diamondback moth, *Plutella xylostella*, and plaque purified three times on *Heliothis virescens* cells. Microscopically, the virus isolated from infected larvae is occluded in many multiple units into a proteinaceous crystal or occlusion body (OB). In contrast with other known baculoviruses, the PxMNPV is highly effective against *P. xylostella*. Furthermore, the PxMNPV is infective not only for its homologous host, but also for a variety of other insect pests.

The above-mentioned PxMNPV of this invention has been deposited under the Budapest Treaty in the American Type Culture Collection (12301 Parklawn Drive, Rockville, Md., 20852, USA) on Sep. 27, 1996, and has been assigned Deposit No. ATCC VR-2543.

For the purpose of this invention, any isolate or clone of *Plutella xylostella* multiple nuclear polyhedrosis virus (PxMNPV) having the identifying characteristics of ATCC VR-2543 and which retain the ability to infect insect pests, particularly *P. xylostella*, are effective.

Mass production of the PxMNPV may be accomplished using either conventional in vivo or in vitro techniques. In either case, the virus that is harvested is in the form of the occlusion bodies (OB) which are produced in the host, as well as in cell culture. In the instance of in vivo production, the virus is typically propagated in larvae of susceptible insect species, such as the *P. xylostella, Heliothis virescens, Helicoverpa zea, Trichoplusia ni, Spodoptera frugiperda, Heliothis subflexa,* and *Spodoptera exigua*. However, *T. ni, H. virescens,* and *P. xylostella* are preferred since they are the most susceptible hosts. Briefly, larvae of the host insect are reared on a conventional artificial diet and treated with a suspension of PxMNPV occlusion bodies. Infected larvae are collected, usually upon death or prior to liquefaction in about 2–5 days, homogenized, and filtered to remove course particulates. The resulting homogenate may then be centrifuged to sediment large debris, the supernatant discarded, and the sediment suspended in sterile water or other carrier and the centrifugation repeated. An appropriate cell lytic agent such as sodium deoxycholate may be added to the suspension during the process to remove any contaminating bacteria and cells. The final washed suspension containing PxMNPV OB may be retained and stored for subsequent use. By way of example, in vivo propagation processes which are suitable for use herein are described in detail by Hosteter and Puttler (U.S. Pat. No. 4,911,913), the contents of which are incorporated by reference herein.

Although the virus may be propagated in vivo as described, such techniques are generally susceptible to contamination and are labor intensive. Therefore, in the preferred embodiment, the virus is produced in cell culture. In vitro mass production of the virus may be accomplished using conventional techniques, such as described by McIntosh (U.S. Pat. No. 5,405,770, issued Apr. 11, 1995), or McIntosh and Ignoffo (1989, J. Invertebrate Pathology, 54:97–102), the contents of each of which are incorporated by reference herein. In accordance with this method, cells of an appropriate insect cell line, are provided in a conventional culture medium, and inoculated with PxMNPV extracellular virus (ECV). Sources of inoculum or inocula include, for example, infectious hemolymph (containing ECV) collected by bleeding an infected insect at approximately 2 days post infection, or virus liberated from OB by alkali treatment. Of course, once a cell line has been infected, ECV may be collected as described hereinbelow and used to infect fresh cell cultures. A variety of insect cell lines are suitable for use herein, including but not limited to, *Heliothis subflexa* (BCIRL-HS-AM1) (McIntosh, U.S. Pat. No. 5,405,770), *Plutella xylostella* (BCIRL-PxEM1) (Kariuki, C., 1996, PhD thesis), *Spodoptera frugiperda* (IPLB-SF21) (Vaughn et al., 1977, In Vitro, 13:213–217), *Trichoplusia ni* (TN-CL1) (McIntosh et al., 1974, In Vitro, 10:1–5), *Heliothis viriscens* (BCIRL-HV-AM1) (McIntosh et al., 1981, J. Invertebr. Pathol., 37:258–264), and *Heliothis zea* (BCIRL-HZ-FB33) (McIntosh et al., unpublished). Highest yields of occlusion bodies have been obtained using the *T. ni* cell line (TN-CL1), and its use is therefore preferred. Other Lepidopteran cell lines suitable for use herein may be prepared using techniques conventional in the art. Following inoculation, the cell culture is incubated a sufficient time and under conditions effective to allow production of virus.

During in vitro cell culture both occluded (OB) and free extracellular virus (ECV) are produced, although the relative proportions may vary with the particular cell line used (e.g. TN-CL1 gives the highest proportion of OB). Both ECV and OB are effective as biocontol agents, but the OBS may be more resistant to some environmental factors such as desiccation. The viral agents (ECV and OB) may then be collected or harvested from the culture supernatant using techniques conventional in the art. The virus may be recovered, for example, by centrifugation and concentration of the culture medium supernatant as described by McIntosh and Ignoffo (1981, J. Invert. Pathology, 37:258–264) or Ignoffo and McIntosh (1986, J. Invert. Pathology, 48:289–295), the contents of each of which are incorporated by reference herein. The virus may then be purified by conventional sucrose gradient centrifugation and plaque assay. The culture conditions including cell density, multiplicity of infection, time, temperature, and media are not critical and may be readily determined by the practitioner skilled in the art.

As a practical matter, it is envisioned that commercial formulations of the subject viral pesticidal agent would be prepared directly from cell culture, larval homogenates, or fractions derived from such homogenates, thereby obviating the need to isolate the virus in pure form. Other suitable means could be readily determined by the skilled artisan. Of course, for applications demanding a high degree of specificity, i.e., a high level of predictability of the intended response by both target and nontarget organisms, it would normally be preferred to prepare the formulations from pure or substantially pure virus. For example, it is possible that extraneous substances in the larval material could have an undesirable effect in regard to the intended activity.

The potency of PxMNPV dictates that it be applied in conjunction with a suitable agronomically acceptable carrier or vehicle as known in the art. Without being limited thereto, inert solids such as talc, vermiculite, cellulose or sugars, wettable powders, and inert liquids such as water or vegetable oils, are illustrative of suitable chemical carriers. The virus may also be formulated in combination with conventional additives such as adherents, insect attractants (i.e., an attracticide), surfactants, wetting agents, UV stabilizers, or other biological control agents or chemical insecticides to increase insecticidal activity.

Depending on the substrate, target species, mode of application, and type of response desired, the concentration of virus in the final composition may vary considerably, but typically should be at least about $5 \times 10^{11}$ to $5 \times 10^{12}$ occlusion bodies/acre. Factors such as phytotoxicity toward the treated plant and tolerance of nontarget species can be used by the skilled artisan in determining the maximum level.

In the case of insect pathogens such as viruses, it may be desirable to use biological carriers to distribute the pathogen. Such a biological carrier may be, for example, a species of insect which is closely related to the target species, but which is itself relatively unaffected by the pathogen. In this disclosure, the word "carrier" is defined to include both biological and inert chemical carriers.

The level of virus is administered in an amount effective to induce infection as predetermined by routine testing. Where the ultimate response is pest mortality, an "effective amount" or "pesticidally effective amount" is defined to mean those quantities of virus which will result in a significant mortality rate of a test group as compared to an untreated group. The actual effective amount may vary with the species of pest, stage of larval development, the nature of the substrate, the type of vehicle or carrier, the period of treatment, and other related factors.

To be effective, the virus must be ingested by the insect; therefore, the virus must be applied directly to the target pests, or to the locus or the vicinity of the pest to be controlled. In the case of plants infested with the target pest, the virus will typically be applied to the plant surfaces, such as the foliage, by spraying or dusting.

The viral pesticide encompassed herein is effective in controlling a variety of insects. Without desiring to be limited thereto, pests of particular interest known to be vulnerable to treatment are agronomically important insects, especially those of the order Lepidoptera, and specifically the diamondback moth (*Plutella xylostella*), the tobacco budworm (*Heliothis virescens*), the corn earworm (*Helicoverpa zea*), the cabbage looper (*Trichoplusia ni*), the beet armyworm (*Spodoptera exigua*), *Heliothis subflexa*, and the fall armyworm (*Spodoptera frugiperda*).

The following examples are intended only to further illustrate the invention and are not intended to limit the scope of the invention which is defined by the claims.

EXAMPLE 1

Restriction Endonuclease Analysis

DNA from PxMNPV was compared with those from the following baculoviruses: *Autographa californica* (AcMNPV), *Anagrapha falcifera* AfMNPV), *Heliothis zea* (HzSNPV), *Helicoverpa armigera* (HaMNPV), and *Anticarsia gemmatalis* (AgMNPV). The DNA from each virus was subjected to restriction endonuclease analysis using four different enzymes: HindIII, XhoI, BstIIE, and BamHI. Enzyme digestion profiles were prepared and analyzed using conventional techniques such as described in McIntosh and Ignoffo (1986, Intervirology, 25:172–176), the contents of which are incorporated by reference herein. Upon comparison, the digestion profiles demonstrated that PxMNPV DNA profiles differed from those of all other viruses, especially in the restriction fragment length polymorphism (RFLP) generated by HINDIII and BamHI.

In addition, hybridization studies of the DNA from the baculoviruses were conducted using a non-radioactive labeled probe of PxMNPV DNA. The results showed that the PxMNPV was distinctive, although related to AcMNPV.

EXAMPLE 2

Neutralization Tests

The PxMNPV was compared with AcMNPV and AfMNPV using an antibody neutralization assay. Various dilutions of AcMNPV-rabbit antiserum shown in Table 1 were mixed with several dilutions of each virus and incubated for 2 hr at 28° C. Treated samples were then inoculated into cultures of susceptible cells, incubated, and examined at 7 days post-inoculation. The complete neutralization of the infectivity of a virus isolate by a high dilution of known antiserum indicates that the isolate is identical to or very closely related to the virus that was used to prepare the antiserum. The highest dilution of antiserum that results in no CPE (production of OBs) is considered as the neutralizing titer.

The results are shown in Tables 1a, b, and c. No cytopathic effect (CPE), i.e. absence of production of OBs in inoculated cells, indicates that the virus has been neutralized by the antibody. As shown in Table 1a, at the $10^3$ TCID$_{50}$ dosage the neutralizing titer of AcMNPV is 1:512, whereas the neutralizing titer of PxMNPV is 1:8 (Table 1b). On the other hand, AfMNPV, which is a variant of AcMNPV, has a neutralizing titer of 1:256 (Table 1c), confirming its close relatedness to AcMNPV

EXAMPLE 3

Insect Cell Culture

Six different Lepidopteran cell lines were compared for their ability to grow and replicate PxMNPV. The cell lines employed were *Heliothis subflexa* (BCIRL-HS-AM1) (McIntosh U.S. Pat. No. 5,405,770), *Spodoptera frugiperda* (IPLB-SF21) (Vaughn et al., 1977, In Vitro, 13:213–217), *Trichoplusia ni* (TN-CL1) (McIntosh et al., 1974, In Vitro, 10:1–5), *Plutella xylostella* BCIRL-PxEM1 (Kariuki, C., 1996, PhD thesis), *Heliothis virescens* (BCIRL-HV-AM1) (McIntosh et al., 1981, In Vitro, 17:649–650), and *Heliothis zea* (BCIRL-HZ-FB33) (McIntosh et al., unpublished). In vitro culture studies were conducted as described in McIntosh (U.S. Pat. No. 5,405,770) or McIntosh (1991, J. Invertebr. Pathol., 57: 441–4421) the contents of each of which are incorporated by reference herein.

A clone of PxMNPV was used to inoculate cultures of all cell lines. The inoculated cells were incubated at a temperature of 28° C. for 7 days in TC199-MK media containing 10% fetal bovine serum, and penicillin and streptomycin. Viral titers (TCID$_{50}$) were assayed using TN-CL1 cells as the indicator cell line and OB were enumerated as previously described by McIntosh et al. [1985, Intervirology 23: 150–156, and 1989, J. Invertebrate Pathology, ibid], the contents of each of which are incorporated by reference herein.

All of the six cell lines were susceptible to PxMNPV, with TN-CL1 producing the highest number of OB/cell.

EXAMPLE 4

Bioassays

PxMNPV was compared with two other baculoviruses, AcMNPV and AfMNPV, for its effectiveness against seven Lepidopteran pests using the standard bioassay test as described by Ignoffo (1966, J. Invertebr. Pathol., 8:531–536) and Ignoffo et al. (1974, Environmental Entomol., 3:117–19), the contents of each of which are incorporated by reference herein. Effectiveness against the following pests was examined: the diamondback moth (*Plutella xylostella*), the tobacco budworm (*Heliothis virescens*), the corn earworm (*Helicoverpa zea*), the cabbage looper (*Trichoplusia ni*), the beet armyworm (*Spodoptera exigua*), *Heliothis subflexa*, and the fall armyworm (*Spodoptera frugiperda*). Twenty-four hr old larvae of each species were placed on artificial diet surfaces inoculated with various concentrations of OBs in a continuous feeding assay. Mortality of the larvae was recorded on a daily basis, and used to calculate the dose necessary to kill 50% of the insects (LC$_{50}$) as well as the time taken to achieve 50% mortality (LT$_{50}$).

The results are shown in Tables 2a, b and c. As shown in Table 2a, PxMNPV was the most effective baculovirus against *P. xylostella*, requiring an LC$_{50}$ dosage of only 5.54 OB/cm$^2$. In contrast, the LC$_{50}$ values for AcMNPV and AfMNPV against *P. xylostella* were 11,600 OB/cm$^2$ (Table 2b) and 9,224 OB/cm$^2$ (Table 2c), respectively. With respect to the other insect pests examined, PxMNPV was also effective as compared with AcMNPV and AfMNPV. In addition, PxMNPV was the most effective against another major pest in the western and southwestern U.S., the beet armyworm (*S. exigua*). The LC$_{50}$ values for the three baculoviruses against this pest were 69.61 OB/cm$^2$ (PxMNPV), 200.84 OB/cm$^2$ (AcMNPV), and 167.59 OB/cm$^2$ (AfMNPV) (Tables 2a, b, and c).

The lethal time-fifty (LT$_{50}$) values for PxMNPV, AcMNPV, and AfMNPV against *P. xylostella* were 6 days, 100 days (extroplated), and 32 days (extroplated), respectively, indicating that PxMNPV killed the diamondback moth larvae faster than the other baculoviruses. A faster kill translates into less damage to treated plants by the insect pest.

It is understood that the foregoing detailed description is given merely by way of illustration and that modification and variations may be made therein without departing from the spirit and scope of the invention.

TABLE 1

Neutralization reactions of three different baculoviruses by *Autographa californica* Multiple Nuclear Polyhedrosis Virus Rabbit Antiserum

| Anti-serum Dilution | Virus Titer ($TCID_{50}$/ml) $10^5$ | $10^4$ | $10^3$ | $10^2$ |
|---|---|---|---|---|
| a) AcMNPV(wt)/AcMNPV-antiserum | | | | |
| 1:8 | -- | -- | -- | -- |
| 1:16 | -- | -- | -- | -- |
| 1:32 | [--] | -- | -- | -- |
| 1:64 | ++ | -- | -- | -- |
| 1:128 | ++ | [--] | -- | -- |
| 1:256 | ++ | -+ | -- | -- |
| 1:512 | ++ | ++ | [--] | -- |
| 1:1024 | ++ | ++ | -+ | -- |
| 1:2048 | ++ | ++ | ++ | -- |
| 1:4096 | ++ | ++ | ++ | -- |
| 1:8192 | ++ | ++ | ++ | -- |
| Control | ++ | ++ | ++ | -- |
| b)PxNPVCl1/AcMNPV-antiserun | | | | |
| 1:8 | ++ | -+ | [--] | -- |
| 1:16 | ++ | ++ | -+ | -- |
| 1:32 | ++ | ++ | -+ | [--] |
| 1:64 | ++ | ++ | -+ | -+ |
| 1:128 | ++ | ++ | ++ | -+ |
| 1:256 | ++ | ++ | ++ | -+ |
| 1:512 | ++ | ++ | ++ | -+ |
| 1:1024 | ++ | ++ | ++ | ++ |
| 1:2048 | ++ | ++ | ++ | ++ |
| 1:4096 | ++ | ++ | ++ | ++ |
| 1:8192 | ++ | ++ | ++ | ++ |
| Control | ++ | ++ | ++ | ++ |
| c) AfNMPVCl1/AcMNPV-antiserum | | | | |
| 1:8 | -- | -- | -- | -- |
| 1:16 | [--] | -- | -- | -- |
| 1:32 | +- | [--] | -- | -- |
| 1:64 | ++ | +- | -- | -- |
| 1:128 | ++ | +- | -- | -- |
| 1:256 | ++ | +- | [--] | -- |
| 1:512 | ++ | ++ | +- | -- |
| 1:1024 | ++ | ++ | +- | -- |
| 1:2048 | ++ | ++ | +- | -- |
| 1:4096 | ++ | ++ | +- | -- |
| 1:8192 | ++ | ++ | +- | -- |
| Control | ++ | ++ | +- | -- |

+ OB present
−No OB
[--] Neutralizing titers at various virus dosages

TABLE 2

Susceptibility of the various lepidopteran larval neonates to baculoviruses

| Insect | Slope ± SE | $LC_{50}$ (95% FL)[a] | RR[b] |
|---|---|---|---|
| a) PxMNPVCL3 | | | |
| *Plutella xylostella* | 0.60 ± 0.03 | 5.54 (3.10–8.91) | — |
| *Helicoverpa zea* | 0.88 ± 0.03 | 36.79 (26.37–50.85) | 6.64 |

TABLE 2-continued

Susceptibility of the various lepidopteran larval neonates to baculoviruses

| Insect | Slope ± SE | $LC_{50}$ (95% FL)[a] | RR[b] |
|---|---|---|---|
| *Heliothis subflexa* | 1.38 ± 0.05 | 24.06 (18.53–30.87) | 4.34 |
| *Heliothis virescens* | 1.39 ± 0.05 | 6.38 (4.96–8.12) | 1.15 |
| *Trichoplusia ni* | 1.17 ± 0.04 | 7.36 (5.49–9.67) | 1.33 |
| *Spodoptera frugiperda* | 0.57 ± 0.03 | 576.53 (331.27–1186.48) | 104.07 |
| *Spodoptera exigua* | 2.09 ± 0.09 | 69.61 (55.84–85.45) | 12.56 |
| b) AcMNPV(wt) | | | |
| *Plutella xylostella* | 1.02 ± 0.04 | 11600.22 (8534.89–15776.59) | 4658.63 |
| *Helicoverpa zea* | 1.02 ± 0.04 | 3.06 (2.07–4.27) | 1.23 |
| *Heliothis subflexa* | 1.18 ± 0.04 | 22.12 (16.81–28.86) | 8.88 |
| *Heliothis virescens* | 1.52 ± 0.06 | 4.73 (3.71–5.95) | 1.89 |
| *Trichoplusia ni* | 1.31 ± 0.06 | 2.49 (1.83–3.28) | — |
| *Spodoptera frugiperda* | 1.04 ± 0.05 | 606.72 (435.10–900.31) | 243.66 |
| *Spodoptera exigua* | 1.59 ± 0.06 | 200.84 (161.27–250.94) | 80.66 |
| c) AfMNPVCL1 | | | |
| *Plutella xylostella* | 0.82 ± 0.03 | 9224.48 (6480.63–13229.39) | 3859.6 |
| *Helicoverpa zea* | 0.86 ± 0.03 | 76.23 (54.36–107.19) | 31.89 |
| *Heliothis subflexa* | 1.86 ± 0.08 | 4.29 (3.46–5.28) | 1.79 |
| *Heliothis virescens* | 1.50 ± 0.06 | 3.37 (2.61–4.27) | 1.41 |
| *Trichoplusia ni* | 1.34 ± 0.07 | 2.39 (1.77–3.10) | — |
| *Spodoptera frugiperda* | 1.00 ± 0.04 | 186.31 (137.47–256.14) | 77.95 |
| *Spodoptera exigua* | 1.47 ± 0.06 | 167.59 (131.88–212.46) | 70.12 |

[a]= $OB/cm^2$ (FL = Fiducial Limits)
[b]= Resistance ratio
n= 150

I claim:

1. A viral agent comprising a biologically pure *Plutella xylostella* multiple nuclear polyhedrosis virus having all of the identifying characteristics of ATCC VR-2543.

2. The viral agent of claim 1 wherein said virus is occluded in an occlusion body.

3. An insecticidal composition comprising the virus of claim 1 and an agronomically acceptable carrier.

4. The insecticidal composition of claim 3 wherein said carrier is inert.

5. A method for controlling insects comprising applying an insecticidally effective amount of a biologically pure *Plutella xylostella* multiple nuclear polyhedrosis virus having all of the identifying characteristics of ATCC VR-2543 to the locus of said insects.

6. The method of claim 5 wherein said insects are of the order Lepidoptera.

7. The method of claim 6 wherein said insects are selected from the group consisting of *Plutella xylostella, Helicoverpa zea, Heliothis subflexa, Heliothis virescens, Trichoplusia ni, Spodoptera frugiperda*, and *Spodoptera exigua*.

8. The method of claim 6 wherein said insects are selected from the group consisting of *Plutella xylostella, Helicoverpa zea, Heliothis virescens*, and *Spodoptera exigua*.

* * * * *